US008167863B2

(12) United States Patent
Yow

(10) Patent No.: US 8,167,863 B2
(45) Date of Patent: May 1, 2012

(54) VENTED VIAL ADAPTER WITH FILTER FOR AEROSOL RETENTION

(75) Inventor: D. Gregory Yow, Wake Forest, NC (US)

(73) Assignee: CareFusion 303, Inc., San Diego, CA (US)

( * ) Notice: Subject to any disclaimer, the term of this patent is extended or adjusted under 35 U.S.C. 154(b) by 907 days.

(21) Appl. No.: 11/581,604

(22) Filed: Oct. 16, 2006

(65) Prior Publication Data

US 2008/0172024 A1 Jul. 17, 2008

(51) Int. Cl.
*A61M 5/32* (2006.01)
*A61B 19/00* (2006.01)

(52) U.S. Cl. .......................... 604/406; 604/411; 604/414

(58) Field of Classification Search .................... 604/90, 604/403–416, 333
See application file for complete search history.

(56) References Cited

U.S. PATENT DOCUMENTS 3,316,908 A 5/1967 Burke
3,359,977 A * 12/1967 Burke ........................... 604/406
3,938,520 A 2/1976 Scislowicz et al.
4,133,762 A 1/1979 Visceglia et al.
4,211,588 A 7/1980 Raines
4,475,914 A * 10/1984 Portnoff ........................ 604/414
4,507,113 A * 3/1985 Dunlap ........................... 604/71
4,512,771 A * 4/1985 Norton .......................... 604/324
4,564,054 A 1/1986 Gustavsson
4,588,403 A 5/1986 Weiss et al.
4,619,651 A 10/1986 Kopfer et al.
4,684,365 A 8/1987 Reinicke
4,768,568 A 9/1988 Fournier et al.
4,815,619 A 3/1989 Turner et al.
4,834,152 A * 5/1989 Howson et al. ............... 141/286
4,983,190 A 1/1991 Verrando et al.
5,672,163 A * 9/1997 Ferreira et al. ................ 604/333
5,766,147 A 6/1998 Sancoff et al.
5,778,872 A 7/1998 Fukunaga et al.
6,139,534 A 10/2000 Niedospial, Jr. et al.

(Continued)

FOREIGN PATENT DOCUMENTS

WO WO 2007/042764 A2 * 4/2007

OTHER PUBLICATIONS

International Preliminary Report on Patentability PCT/US2007/022138 mailed Apr. 30, 2009.

(Continued)

*Primary Examiner* — Tatyana Zalukaeva
*Assistant Examiner* — Philip R Wiest
(74) *Attorney, Agent, or Firm* — McDermott Will & Emery LLP

(57) ABSTRACT

A vented vial adapter has a filter attached to a vent arm that includes at least two filter media for suppressing aerosolized medicaments from leaving the vial and suppressing bacteria and other contaminants from entering the vial during reconstitution activities of the medication in the vial. The filter media allows the passage of air to the atmosphere outside the vial for pressure equalization. In another aspect, a third filter medium is used in the vent of the adapter to allow gas to pass in either direction through it, but prevents bacteria and particulate matter in the atmosphere from reaching the second filter device. A first filter is hydrophobic and prevents non-dispersed liquid from reaching the second filter, while conducting liquid dispersed in gas. The second filter absorbs the liquid dispersed in gas.

19 Claims, 6 Drawing Sheets

U.S. PATENT DOCUMENTS

| | | | |
|---|---|---|---|
| 6,343,629 | B1 | 2/2002 | Wessman et al. |
| 6,511,600 | B1 | 1/2003 | Ohtani |
| 6,544,246 | B1 | 4/2003 | Niedospial, Jr. |
| 6,875,205 | B2 | 4/2005 | Leinsing |
| 2001/0029360 | A1 | 10/2001 | Miyoshi et al. |
| 2005/0031229 | A1 | 2/2005 | Tang |
| 2006/0106360 | A1 | 5/2006 | Wong |

OTHER PUBLICATIONS

PCT International Search Report for International Application No. PCT/US2007/022138 mailed Feb. 5, 2008.

"Comparison of Water Filter/Purification Technologies" Purification Technologies, Mar. 11, 2011, http://www.home-water-purifiers-and-filters.com/water-purification.php.

"Activated Carbon for Drinking Water Filtration" DoultonUSA, Mar. 14, 2011, http://www.doultonuse.com/activated__carbon__water__filtration.htm.

Hasegawa, H. et al., "Membrane filter (pore size, 0.22-0.45 micro m; thickness, 150 micro m) passing-through activity of *Pseudomonas aeruginosa* and other bacterial species with indigenous infiltration ability." FEMS Microbiol Lett. Jun. 6, 2003;223(1):41-6. Department of Applied Biological Chemistry, Faculty of Agriculture, Niigata University, 950-2181, Niigata, Japan.

Catalogue Document: +MSD, Pharmacy Supplies, Dispensing Pins, p. 129, 2003.

Catalogue Documents: Sigma SW 123E Apr. 2005: Cannel Pharma ab, *PhaSeal*, pp. 1-3 and 1-2, Apr. 2005.

Catalogue Document: Chemo Dispensing Pin; B/Braun, B. Braun Medical Inc., IVX02 Rev. 8/00, Aug. 2000.

* cited by examiner

VENTED VIAL ADAPTER WITH FILTER FOR AEROSOL RETENTION

BACKGROUND OF THE INVENTION

The invention is related generally to vial adapters of the type used in the transfer of medical fluids between a vial and another medical fluid container, and more particularly, to vented vial adapters useful for safe reconstitution and withdrawal of cytotoxic medicament from vials.

Access ports for injecting fluid into or removing fluid from a container, such as a drug vial, are well known and widely used. Conventional seals of drug vials generally involve a pierceable rubber stopper formed of an elastomeric material such as butyl rubber or the like, placed in the opening of the vial. A closure, typically formed of metal, is crimped over the rubber stopper and the flange of the vial to positively hold the stopper in place in the opening of the vial. The closure has an outer size, known as a “finish size.” A sharp cannula is inserted through the rubber stopper to position the distal, open end of the cannula past the rubber stopper to establish fluid connection with the interior of the vial. In the case of certain medications, such as those used for chemotherapy or nuclear medicine, the rubber stopper is made thicker so that increased protection is provided against leakage.

Vial adapters have been found useful in that they can attach the sharpened cannula that is used to pierce the stopper and move far enough into the vial interior to establish fluid communication with the vial, to the connection device of another fluid container or fluid conduction device. For example, the adapter may include a female Luer fitting opposite the sharpened cannula to receive the male luer of a syringe. The “adapter” therefore adapts the vial to the syringe, or adapts the sharpened cannula to the male luer of the syringe.

It has also been found useful in some applications to provide a means to attach or anchor the adapter to the vial to hold it in place while fluid communication between the vial and another device proceeds so that inadvertent disengagement of the adapter from the vial does not occur. For example, the adapter may have arms that engage the neck or flange of the vial and hold the adapter in place on the vial. Other means include a circular slotted housing that fits around the outside of the vial closure and snaps onto the vial closure under the crimped retaining cap on the under-surface of the vial’s flange thereby grasping the vial neck flange and the underside of the closure. The circular housing typically has a plurality of claws or other retaining devices that are positioned under the flange of the vial opening thereby interfering with removal of the adapter from the vial.

It has also been found useful in some applications to have a valve placed in the adapter to result in a closed system. The valved adapter permits engagement of the sharpened cannula with the contents of the vial without leakage of fluid from the vial through the adapter until the valve is purposely opened via a syringe, for example. Then when the second fluid device has been prepared, it can be connected to the adapter thereby opening or activating the valve that then permits fluid flow between the vial and second fluid device.

Vials made of glass or polymeric materials, the walls of which are non-collapsible, require an air inlet when medical fluid is withdrawn to prevent the formation of a partial vacuum in the vial. Such a partial vacuum inhibits fluid withdrawal from the vial. Typically, adapters for use with such vials have a sharpened cannula that includes both a medicament fluid lumen and a vent lumen therein. The vent fluid lumen provides pressure equalization when fluid is added to the vial or is withdrawn from the vial so that such fluid movement occurs smoothly.

Many medicaments are prepared, stored, and supplied in dry or lyophilized form in glass vials. Such medicaments must be reconstituted at the time of use by the addition of a diluent thereto. Various methods of adding the diluent to the dry or lyophilized medicament have been used over the years. One method that is commonly used is the vial adapter technique in which the diluent that may be contained in a bottle or a syringe is connected to the vial adapter which has a sharpened cannula. Once connected to the diluent container, the sharpened cannula is then forced through the closure and rubber septum of the vial to communicate the diluent to the dry or lyophilized medicament residing in the vial. After reconstitution, the liquid is usually withdrawn from the vial into the intravenous solution bottle or syringe, or other container for administration to the patient through an intravenous (“IV”) administration set or by other means.

For such reconstitution activities, a vented vial adapter is used to avoid any difficulties with a partial vacuum or high pressure inside the vial, as discussed above. These are sometimes known as pressure-equalizing vial adapters. However, with some vented vial adapters this technique is unsatisfactory because both the dry or lyophilized material and the diluent can be exposed to ambient airborne bacterial contamination during withdrawal of the reconstituted medical fluid if a filter is not present in the vial adapter.

During the reconstitution process of certain medical fluids, such as chemotherapy fluids or nuclear medicines, it is also desirable to avoid contamination of the surrounding air resulting from the formation of aerosols or drops in the vial. As used herein, aerosols are suspensions of solid or liquid particles in a gas, such as air. Contamination is possible during the injection of the diluent into the vial because more material is being added to the closed space of the vial and therefore, the vent of the adapter must channel away an equal amount of air from the vial to make room for the additive. If this air removed from the vial is channeled to the outside atmosphere, such contamination can lead to problems, among other things, in the form of allergic reactions in the exposed personnel, especially when the air is contaminated with cytotoxic drugs, chemotherapeutic drugs, anesthetics, media containing isotopes, and allergy inducing substances of various kinds.

It would also be desirable to provide a vented vial adapter for use with non-collapsible containers that is designed to prevent aerosolizing of liquid material into the ambient atmosphere as reconstitution occurs. It is desirable for the person performing the procedures to avoid contacting the medications, especially the inhalation of aerosolized medications. A vial adapter with sufficient venting and filtering is necessary to avoid such aerosolizing.

In prior vented vial adapters, a vent lumen in the sharpened cannula leads to a filter that opposes the entry of particulate matter and bacteria into the vial during medicament withdrawal or aspiration. The filter also opposes venting to the outside atmosphere. A disadvantage of prior devices is their limited ability to retain aerosols of medicament. Typical adapters employ a membrane filter formed with a pore size of about 0.2 microns. Aerosols of many medications are known to pass through such filters.

Hence, those skilled in the art have recognized a need for a pressure-equalizing vial adapter having a filter for preventing bacteria and other contaminants from reaching the contents of the vial during withdrawal of the reconstituted contents of the vial contents, and having improved aerosol retention capability so that reconstituted contents of the vial that become aerosolized do not escape the vial to the ambient environment. The present invention fulfills these needs and others.

SUMMARY OF THE INVENTION

Briefly and in general terms, the present invention is directed to a system and a method for use in reconstituting medicaments in rigid vials in which a filter is provided to inhibit the communication of aerosols of the vial medicament from leaving the vial and entering the surrounding atmosphere.

In accordance with more detailed aspects, there is provided a vented vial adapter for retaining aerosols when accessing a vial having a pierceable seal located over an opening of the vial, the adapter comprising a cannula having a medicament lumen and a vent lumen, the cannula having a relatively sharp tip to pierce the seal of the vial, a body portion having a medicament port in fluid communication with the medicament lumen of the cannula, the medicament port configured to allow liquid to be introduced into and removed from the vial and a vent port in fluid communication with the vent lumen of the cannula, the vent port configured to allow passage of filtered air to and from an atmosphere outside the vial, thereby allowing air pressure in the vial to equalize with the outside atmosphere when liquid is introduced into and removed from the vial, a first filter device disposed between the vent lumen of the cannula and the vent port, the first filter device configured to allow passage of liquid dispersed in gas while blocking non-dispersed liquid, and a second filter device disposed between the first filter device and the vent port, the second filter device configured to absorb liquid dispersed in gas.

In further, more detailed, aspects the first filter device comprises pores having a first pore size, and the second filter device comprises pores having a second pore size that is different than the first pore size. The first filter is hydrophobic and has a pore size selected to prevent the passage of liquid through the first filter, whereby the first filter prevents wetting out the second filter. The second filter device comprises a desiccant configured to absorb liquid particles. The second filter device comprises a molecular sieve having pores sized to trap liquid particles. The vial adapter of claim 1 wherein the second filter device comprises pores having a polar surface adapted to attract polar molecules.

In a further detailed aspect, the vial adapter of further comprises a third filter device disposed between the second filter device and the vent port, the third filter device configured to inhibit the passage of bacteria.

In accordance with other aspects, there is provided a vented vial adapter for retaining aerosols when accessing a vial having a pierceable seal located over an opening of the vial, the adapter comprising a flexible attachment device configured to engage the vial for secure mounting of the vial adapter to the vial, a cannula on the attachment device, the cannula having a sharpened tip configured to pierce the seal of the vial, a vent opening adjacent the sharpened tip, a slot, and a medicament opening on the slot, the vent opening leading to a vent lumen extending through the cannula, the medicament opening leading to a medicament lumen extending through the cannula, a body portion having a valve in fluid communication with the medicament lumen of the cannula, the valve biased to a closed orientation and configured to allow liquid to be introduced into and removed from the vial when the valve is actuated to an open orientation, and an elongate filter chamber having a first opening and a second opening, the first opening in fluid communication with the vent lumen of the cannula, the filter chamber containing a first filter device and a second filter device, the first filter device disposed between the first opening and the second filter device and configured to allow passage of liquid dispersed in gas to the second filter device while blocking non-dispersed liquid, the second filter device disposed between the first filter device and the second opening and configured to absorb liquid dispersed in gas.

In more detailed aspects, the first filter device comprises pores having a first pore size, and the second filter device comprises pores having a second pore size that is different than the first pore size. The first filter is hydrophobic and has a pore size selected to prevent the passage of liquid through the first filter, whereby the first filter prevents wetting out the second filter. The second filter device comprises a desiccant configured to absorb liquid particles. The second filter device comprises a molecular sieve having pores sized to trap liquid particles. The second filter device comprises pores having a polar surface adapted to attract polar molecules. The filter apparatus further comprises a third filter device disposed between the second filter device and the second opening in the filter chamber and configured to prevent passage of bacteria.

In accordance with aspects of a method of the invention, there is provided a method for retaining aerosols when accessing a vial having a pierceable seal located over an opening of the vial, the method comprising piercing the vial seal with a sharp cannula having a medicament lumen and a vent lumen separate from each other, conducting non-dispersed liquid through the medicament lumen of the cannula into the vial, conducting gas out of the vial through the vent lumen and through a vent port in fluid communication with the vent lumen to an atmosphere outside the vial, blocking the passage of non-dispersed liquid out the vent lumen to the outside atmosphere at a first filter device, passing liquid dispersed in gas through the first filter device, and absorbing liquid dispersed in gas at a second filter device disposed between the first filter device and the vent port.

In more detailed method aspects, the step of passing liquid dispersed in gas through the first filter device comprises passing the dispersed liquid through pores in the first filter device having a first pore size, and the step of absorbing liquid dispersed in gas at a second filter device comprises absorbing the dispersed liquid in pores in the second filter device having a second pore size smaller than the first pore size. The step of blocking the passage of non-dispersed liquid out the vent lumen to the outside atmosphere comprises blocking the passage of non-dispersed liquid with a hydrophobic material. The step of blocking the passage of non-dispersed liquid comprises blocking the passage of non-dispersed liquid with a filter material having a pore size selected to prevent the passage of liquid. The step of absorbing liquid dispersed in gas comprises absorbing the dispersed liquid with a desiccant. The step of absorbing liquid dispersed in gas comprises trapping liquid particles in pores of a molecular sieve. The step of absorbing liquid dispersed in gas comprises attracting polar molecules with pores having a polar surface.

In yet further method aspects, the method comprises blocking the passage of bacteria from the atmosphere outside the vial from reaching the vent lumen. The step of blocking the passage of bacteria from reaching the vent lumen comprises a thin membrane of porous material.

These and other aspects, features, and advantages of the present invention will become apparent from the following detailed description of the preferred embodiments which, taken in conjunction with the accompanying drawings, illustrate by way of example the principles of the invention.

DETAILED DESCRIPTION OF PREFERRED EMBODIMENTS

Figure 1:
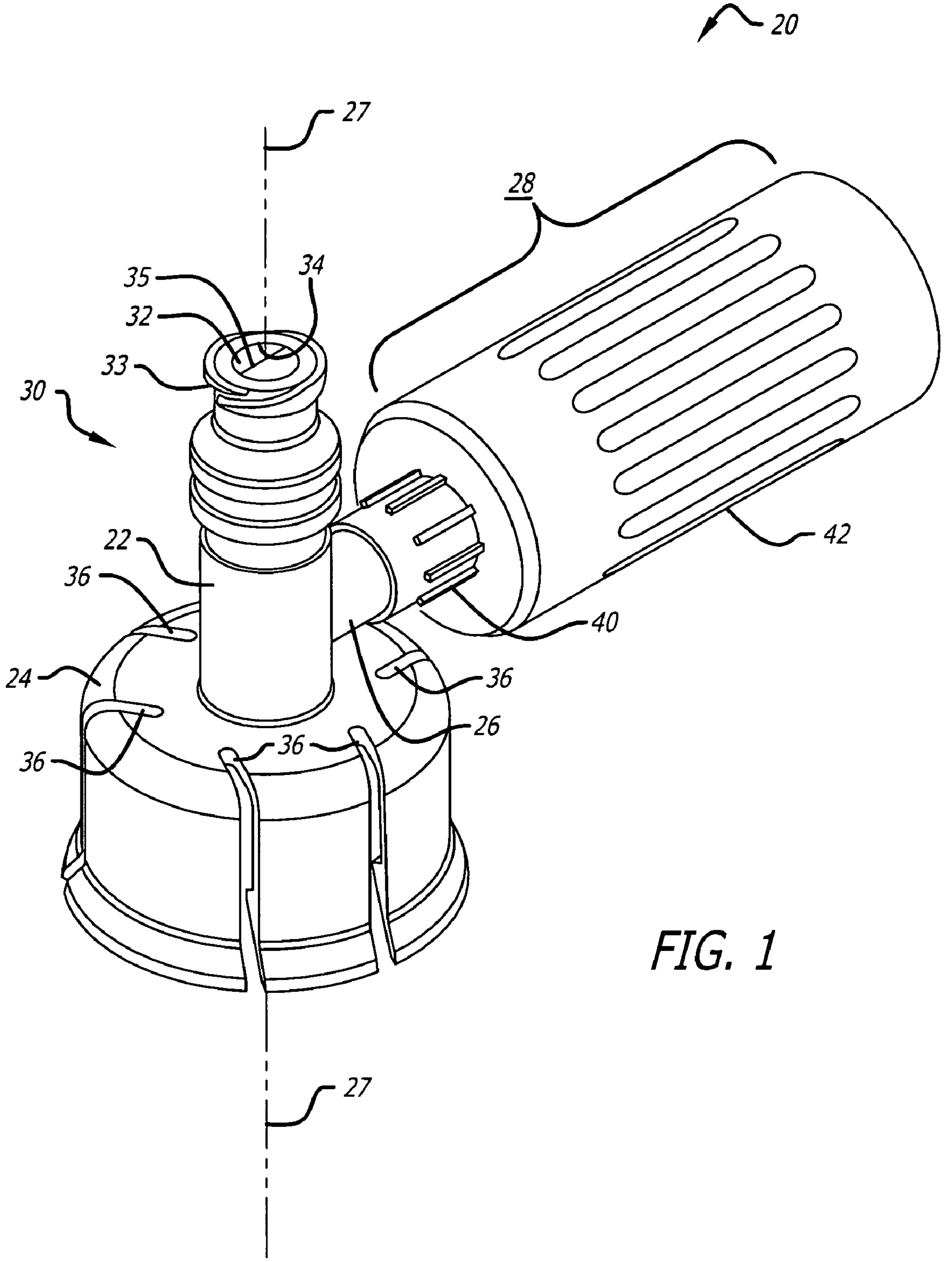
FIG. 1 is a perspective view of a vented vial adapter from the angle of the needle-free valve connector that forms a medicament port to which another medical fluid container may be connected to the adapter, showing also a slotted vial connector housing, a side air vent arm, and a filter for use in equalizing the pressure in a rigid-walled vial during reconstitution of the vial contents and subsequent withdrawal.
Figure 2:
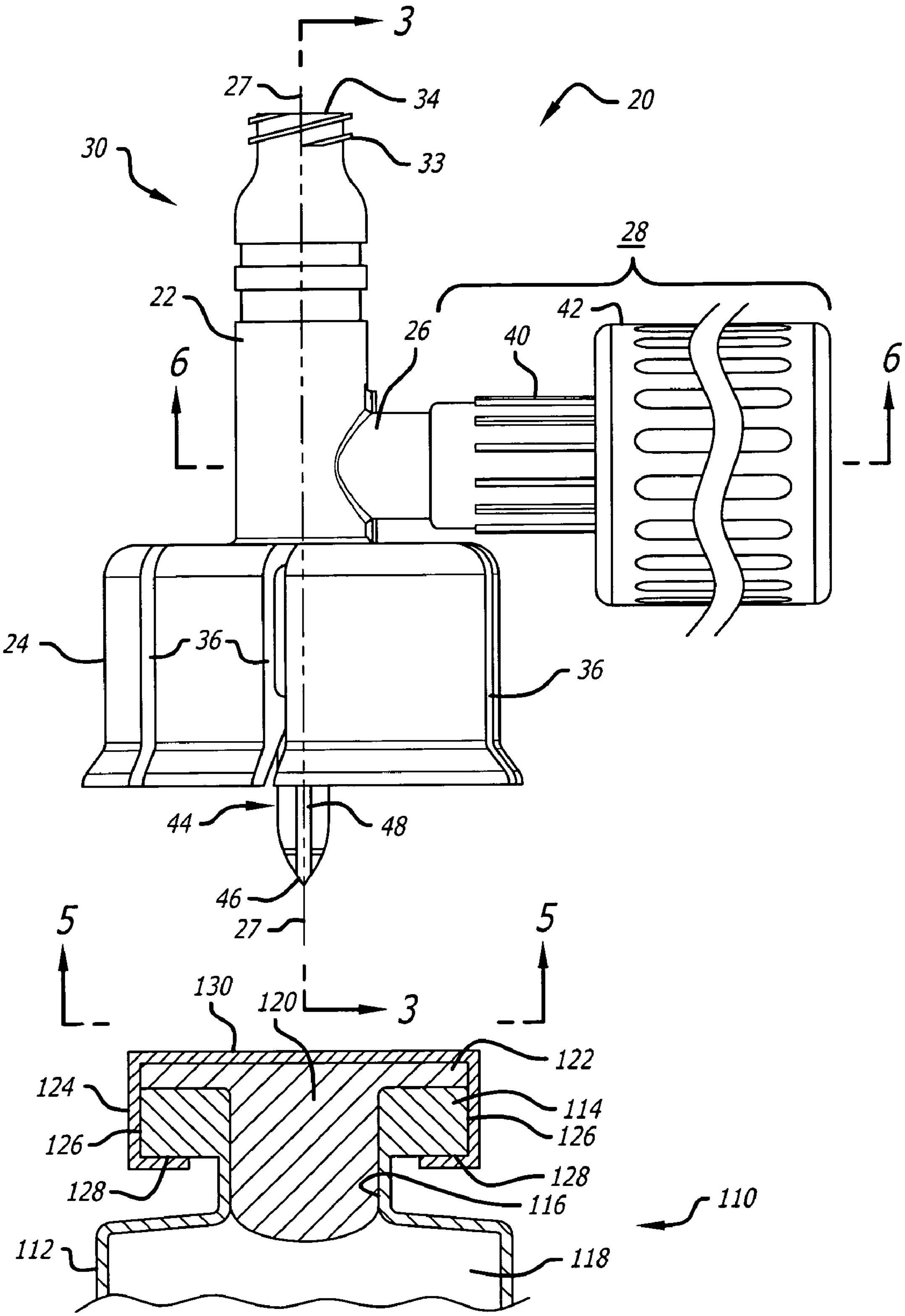
FIG. 2 is a side view of the vial adapter of FIG. 1 positioned above the opening portion of a vial, and showing a cannula having a relatively sharp tip for piercing the septum of the vial while the slotted connector housing becomes attached to the vial flange to thereby securely mount the vial adapter to the vial during the performance of reconstitution and withdrawal activities with the vial.

Referring now to the drawings in more detail in which like reference numerals refer to like or corresponding devices among the views, there is shown in FIGS. 1 and 2 a view of an embodiment of a vial adapter 20 in accordance with aspects of the invention. The vial adapter comprises a body portion 22, a slotted vial attachment housing 24, a vent arm 26 formed at a ninety degree angle to the longitudinal axis 27 of the body portion in this embodiment, a filter apparatus 28, a needle-free valve connector 30 having an internal valve 32, external threads 33 for coupling to a male connector, a female luer connection port 34, and a sharpened cannula 44 for piercing the septa of sealed vials. The needle-free valve connector 30 may take different forms. One form is the SmartSite valve connector from the ALARIS Products division of Cardinal Health, San Diego, Calif. Details on the construction and operation of such a connector are located in U.S. Pat. No. 5,676,346 to Leinsing, incorporated herein by reference.

Referring in more detail to FIG. 2, a part of a vial 110 is also shown. The vial includes a rigid wall 112 that does not expand or collapse as fluid is being introduced to the vial or fluid is withdrawn from the vial, respectively. The vial includes a vial flange 114 with an opening 116 that permits access the internal chamber 118 of the vial. In this view, the opening of the vial is sealed with a septum 120 that includes a septum flange 122 covering a portion of the vial flange. Securing the septum in place is a crimped closure 124 that is formed over the septum on the top of the vial flange, extending around the outer surface 126 of the vial flange, and crimped to the undersurface 128 of the vial flange thereby securely retaining the septum in position to seal the opening of the vial. The closure includes a port 130 through which a sharpened cannula may be forced to make fluid communication with the internal chamber of the vial. In the case of FIG. 2, the sharpened cannula 44 of the vial adapter 20 positioned above the vial 110 may be used. Even though FIG. 2 is not drawn to scale, it will be noted that the vial attachment housing 24 is sized to fit over the vial flange 114 while the cannula extends into the vial inner chamber 118 for fluid communication. The slots 36 enable the housing to flex outward thereby expanding to accept the vial flange and closure 124. For further details on the slotted housing 24 for connecting to vials, see U.S. Pat. No. 6,875,205 to Leinsing, incorporated herein by reference.

Figure 3:
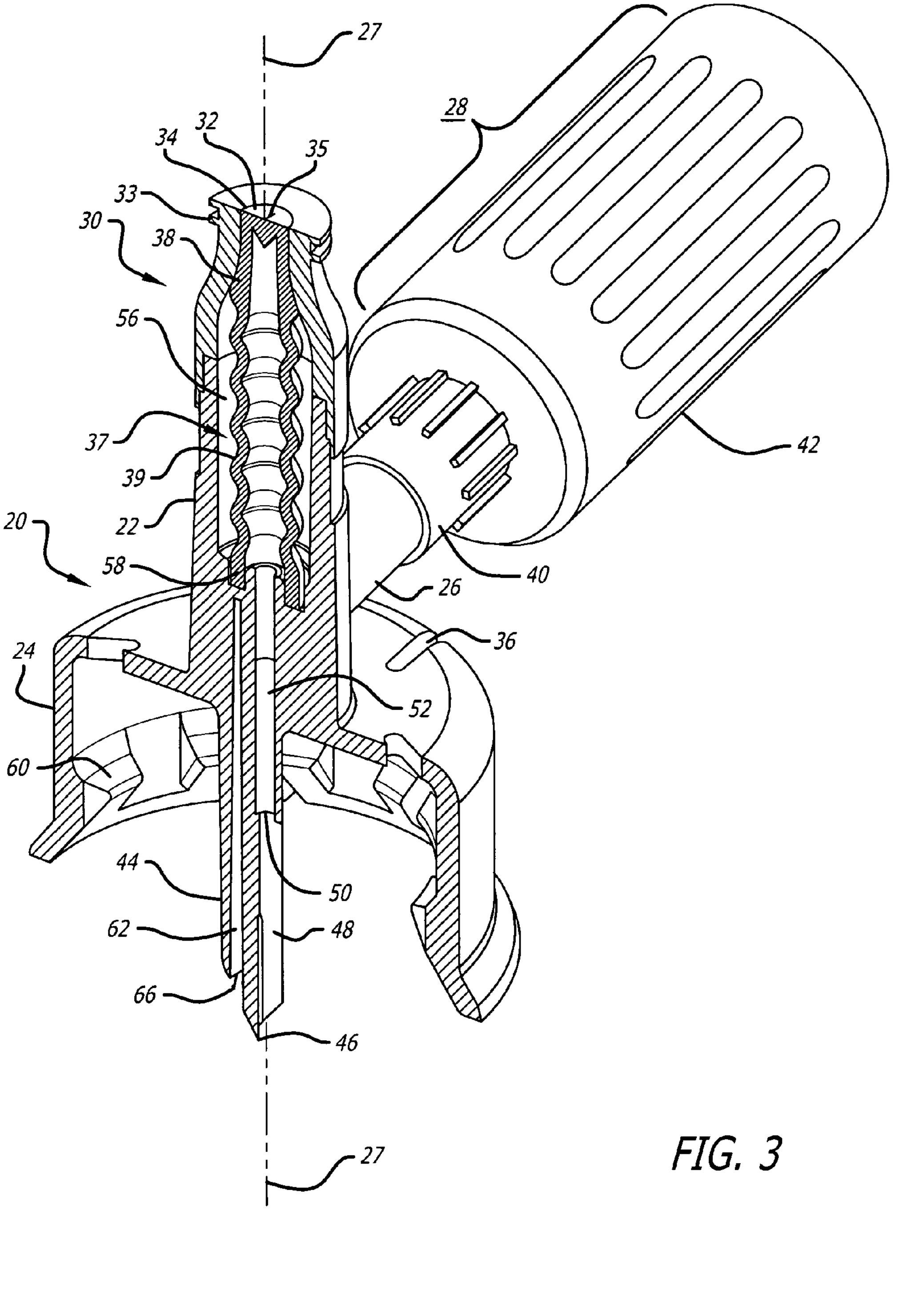
FIG. 3 illustrates a perspective, cross-sectional view of the vial adapter of FIGS. 1 and 2 rotated approximately 45° showing a medicament lumen extending through the sharpened cannula and a body portion of the housing, and showing a limited view of a vent lumen through the sharpened cannula and body portion.

In the illustrated embodiment of FIG. 3 shown in cross-section, the needle-free connector 30 includes an elastomeric, resilient piston 37 having a piston head 38 attached to a spring section 39. The spring section biases the piston head into the closed configuration shown in FIG. 3. The piston head includes a naturally-open bore 35 that is naturally open and self-opens when the piston head is pushed into the larger diameter 56 section of the body 22. This action also causes the spring section of the piston to compress, storing energy to return the piston head to the closed position at which the bore closes.

FIG. 3 also shows the filter apparatus 28 in perspective and is described below in relation to FIGS. 4, 5, and 10 in greater detail. The filter apparatus has a filter stem 40 that fits over the side vent arm 26 of the body member 22 and an elongate filter chamber 42 oriented at an angle from the longitudinal axis 27 of the body member. The side vent arm of the body may be at different angles than that shown and the connection of the filter apparatus to the side arm may take other configurations than that shown. As shown in FIG. 3, the valve 32 is in fluid communication with the cannula 44 that is oriented along the longitudinal axis 27 within the vial attachment housing 24. The cannula enters the internal space 118 of the vial 110 (FIG. 2) when the housing is pressed onto a vial, as described above. An open channel or slot 48 is formed in the cannula in this embodiment to guide fluid to the valve 32 and to permit an acceptable flow rate of the medicament when the valve is in its open orientation.

In the cross-sectional perspective view of FIG. 3 a medicament opening 50 in the sharpened cannula 44 is located adjacent the open channel or slot 48 formed in the cannula. The medicament opening is part of a medicament lumen 52 extending through the sharpened cannula and the body portion 22. The medicament lumen is in fluid communication with the valve 32. Adjacent the valve is an enlarged cylindrical cavity 56 formed in the body portion. In this cavity, a circular groove 58 is formed to retain one end of the piston 38. Also shown in FIG. 3 is an anchor device 60 in the form of claws for grasping the underside of a vial flange 114 (FIG. 2) to securely retain the vial adapter 20 to the vial 110.

The cross-sectional view of FIG. 3 permits closer inspection of the medicament opening 50 and the medicament lumen 52 in the cannula 44. It can be seen that the medicament opening is approximately perpendicular to the longitudinal axis 27 of the cannula. To allow enough fluid access to the opening 50 so that an adequate medicament flow rate can be obtained, the open channel or slot 48 has been formed in the side of the cannula from the sharp tip 46 to the medicament opening 50 so that more fluid may flow through the medicament opening.

Although not shown completely, a vent lumen 62 can be seen. The vent lumen is separate from the medicament lumen 52 in this embodiment. A vent lumen opening 66 on the cannula 44 is visible at the sharpened tip 46 of the cannula in this embodiment.

Figure 4:
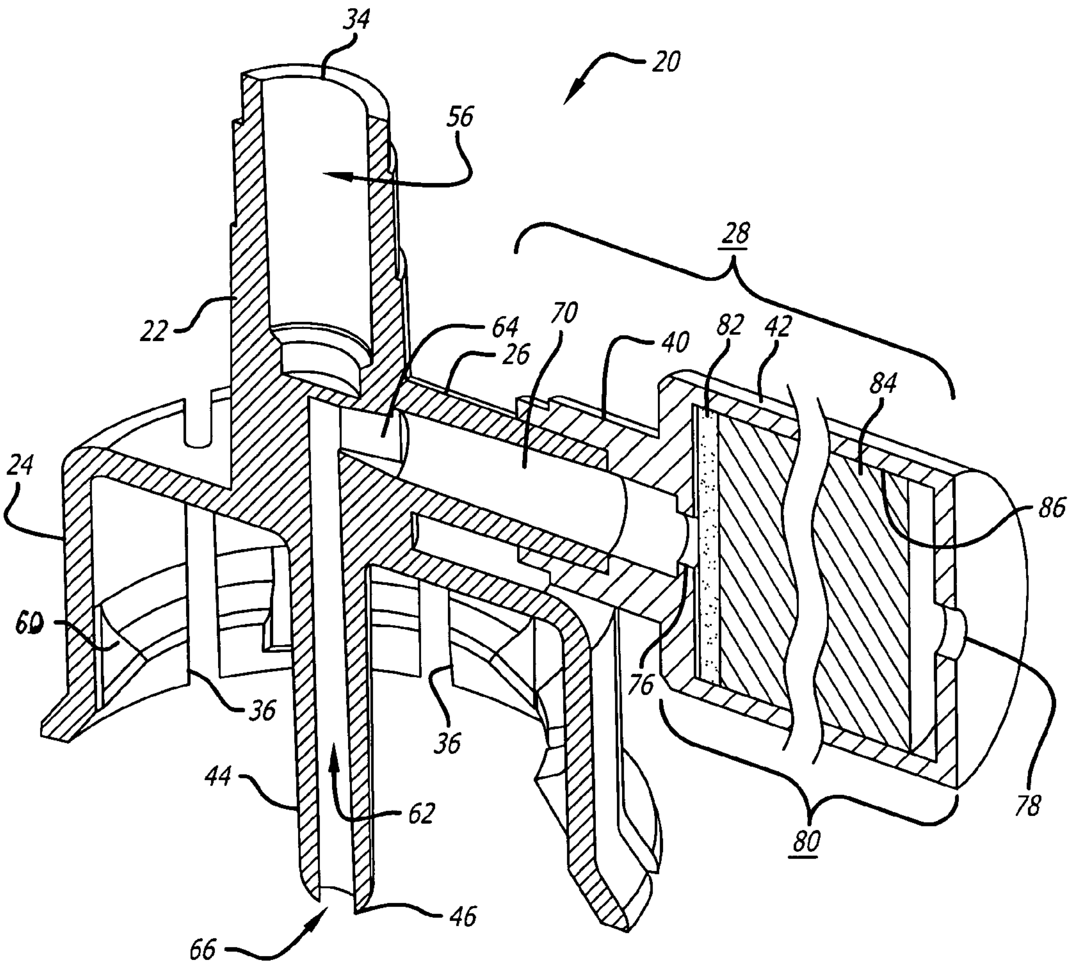
FIG. 4 is a perspective, cross-sectional view of a vial adapter shown in FIGS. 1 and 2 rotated approximately 20° in the direction opposite the rotation of FIG. 3, showing the vent lumen proceeding through the sharpened cannula and the body portion, and showing a cross-sectional view of the vent arm, and filter apparatus mounted to the vent arm having a first opening, a second opening, a first filter device disposed between the first and second openings, and a second filter device disposed between first filter device and the second opening.

FIG. 4 presents a clearer view of the path of the vent lumen 62 through the vial adapter 20. In this embodiment, the piston and valve have been removed for clarity of illustration of the vent system. A mounting structure 63 for the needle free connector 30 (not shown) forms a part of the body portion 22 in this embodiment. The body portion 22 includes a right angle vent lumen portion 64 leading to a larger vent cavity 70 in the vent arm 26. The filter apparatus 28 is mounted over the vent arm in a secure fashion so that any fluid that moves through the vent pathway of the vial adapter must be filtered by the filter apparatus. The construction and operation of the filter apparatus is described in further detail below.

Figure 5:
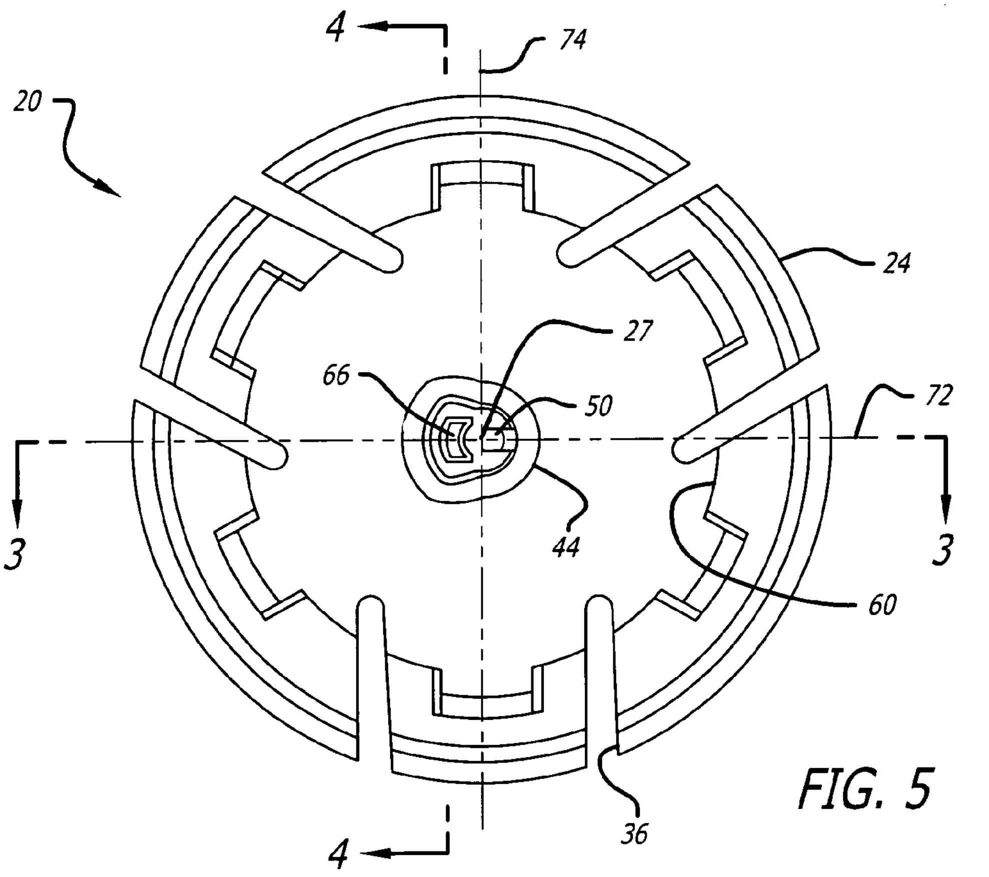
FIG. 5 is a bottom view of the vial adapter of FIGS. 1 and 4 showing a plan view of the sharp tip of the cannula revealing the openings of the vent and medicament lumina.

Continuing with further details of the construction of the vial adapter housing 24 in this embodiment, FIG. 5 presents a plan view of the bottom of the vial adapter of FIGS. 1-4 with the filter apparatus 28 removed for clarity and ease of illustration. Shown on the cannula 44 are the vent opening 66 and the medicament opening 50 in relation to radial centerlines 72 and 74 of the housing. The medicament opening and the vent opening reside on a common centerline 72. The intersection of the centerlines 72 and 74 marks the longitudinal axis 27 (FIGS. 1 and 2) extending perpendicular to the plane defined by the two centerlines. It will be noted that the medicament opening resides on the longitudinal axis 27 although in another embodiment, this may not be the case.

Figure 6:
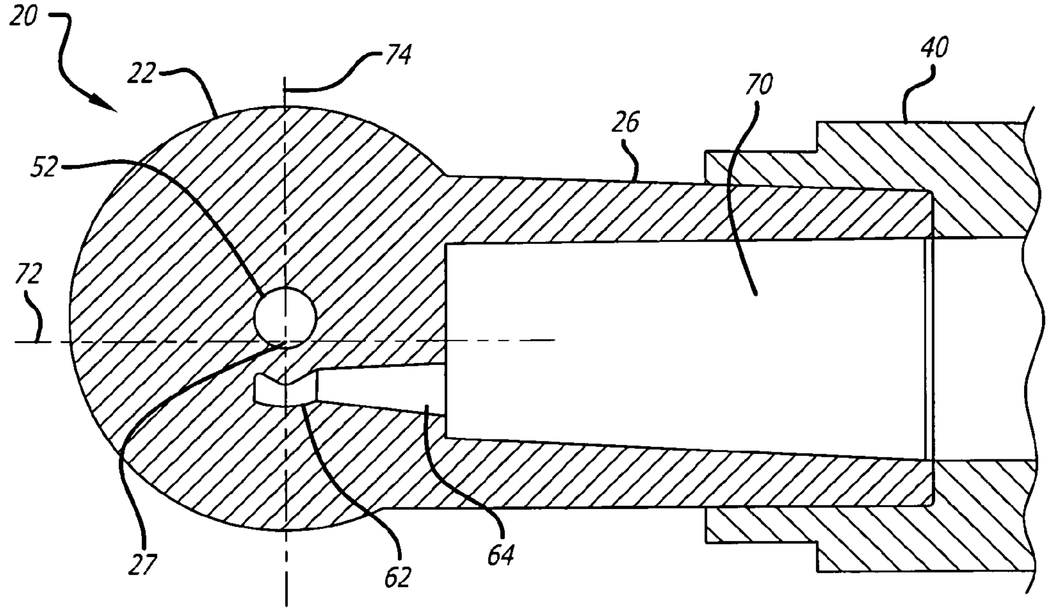
FIG. 6 is a cross-sectional view of the body portion of the vial adapter of FIGS. 1 through 4 showing the locations of the medicament and vent lumina and their respective cross-sectional sectional shapes, as well as showing the internal shape of the chamber in the vent arm of the body portion.

FIG. 6 presents a cross-section view of portions of the medicament lumen 52 and vent lumen 62. Also visible is the right angle vent lumen portion 64 and the vent cavity 70 located in the vent arm 26. The figure also shows the centerlines 72 and 74. It will be noted that in this embodiment, the cross-sectional shape of the medicament lumen 52 is circular and is located on the longitudinal axis 27 although it is not centered on the axis. On the other hand, the cross-sectional shape of the vent lumen 62 is, in general, a polygon having four sides, one of which is generally concave, facing toward the medicament lumen, and the opposite of which is convex, facing away from the medicament lumen. Other shapes and locations of the vent lumen and the medicament lumen are possible as will become apparent to one of skill in the art.

Figure 7:
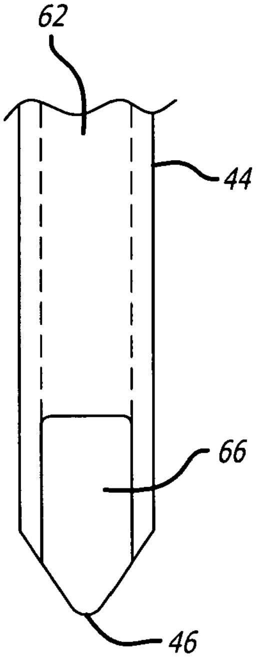
FIGS. 7 through 9 show various rotated side views of the cannula showing the sharp tip in all views, and the vent opening in the cannula in FIGS. 7 and 8 rotated ninety degrees, and an open channel or slot for the medicament opening in FIG. 9.
Figure 8:
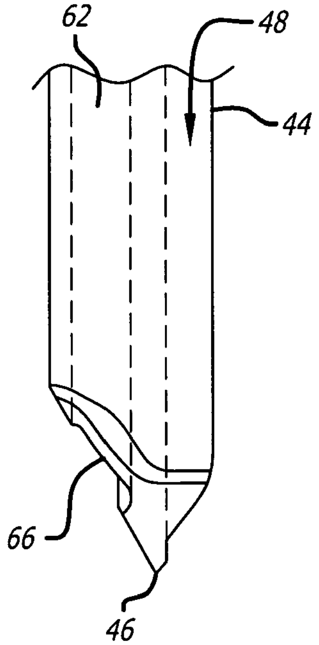
Figure 9:
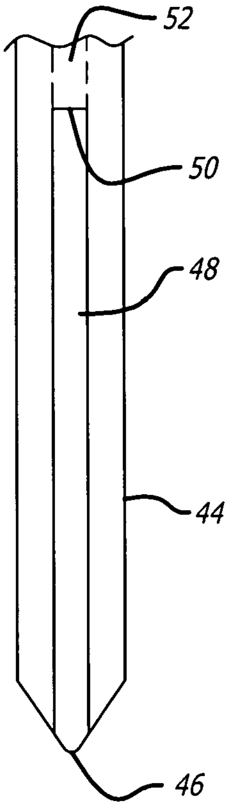

FIGS. 7, 8, and 9 are provided to show side views of an embodiment of the cannula 44 with the two lumina of the medicament 52 and the vent 62, and the relatively sharp tip 46 so that the configurations of the openings of the cannula can be seen. FIGS. 7 and 8 show the vent opening 66 with a rotation of ninety degrees between each figure. The vent opening leads to the vent lumen 62, which extends adjacent the open channel or slot 48, as shown in dashed lines in FIG. 8. FIG. 9 shows the cannula rotated another ninety degrees which is one-hundred and eighty degrees from FIG. 7, so that the open channel or slot 48 formed in the side of the cannula to provide fluid access to the medicament opening 50 on the medicament lumen 52 can clearly be seen. Other shapes, orientations, and locations of openings, slots and channels will become apparent to those of skill in the art.

Returning now to FIG. 4, the filter chamber 42 of the filter apparatus 28 includes a first opening 76 and a second opening 78. The second opening serves as a vent port to the ambient atmosphere outside of a vial secured to the vial adapter 20 during use. The first opening is adjacent the vent cavity 70 of the vent arm 26 and is in fluid communication with the vent lumen 62 of the cannula 44.

The filter chamber 42 has an internal diameter substantially greater than the internal diameter of the vent lumen 62, which allows for greater filtering area and flow capacity. The first and second openings 76 and 78 are separated by a gap 80 in which is contained a first filter device 82 and a second filter device 84. The first filter device is disposed between the first opening 76 and the second filter device, and the second filter device is disposed between the first filter device and the second opening 78.

The outer periphery of the first filter device 82 is attached to the inner cylindrical wall 86 of the filter chamber 42 in this embodiment such that fluids cannot pass around the outer periphery of the first filter device. As used herein, the term "fluid" is used in its common sense and therefore refers to both liquids and gases. However, the first filter device is configured to allow gas, including liquid particles dispersed in the gas, to pass in either direction through the first filter device. The first filter device is further configured to prevent the passage of non-dispersed liquid, that is liquid not dispersed as small particles in gas. As such, aerosolized medicament in the form of droplets of liquid suspended in air may pass through the first filter device while the first filter device blocks larger drops or bodies of liquid medicament from passage through the first filter device.

Preferably, the first filter device 82 is resistant to absorbing liquid or is hydrophobic, which prevents it from clogging easily with liquid. In addition, the first filter device is preferably, though not necessarily, configured to prevent bacteria and other microorganisms in the ambient atmosphere from passing through the first opening 76 and into the vent lumen 62. The first filter device can be a thin membrane or pad of porous material such as, but not limited to, polytetrafluoroethylene (PTFE) and other vinyl polymers.

Preferably the first filter device 82 in this embodiment has a relatively small pore size of at least about 0.2 microns. At about 0.2 microns, pores of the first filter element will block more liquid dispersed in gas, but may reduce the rate at which air pressure inside an attached vial equalizes with the ambient air pressure. A larger pore size of up to about 3 microns may be employed to increase the rate of pressure equalization while still blocking larger sized bacteria, liquid droplets, and other particles. The configuration of the first filter in which it provides a hydrophobic barrier in combination with a small pore size prevents wetting out of the second filter. Particles that flow through the first filter device are retained by the second filter device 84, as described in detail below.

The second filter device 84 is configured to prevent liquid particles dispersed in gas that pass through the first filter device 82 from venting out of the second opening 78 of the filter apparatus 82. To retain the dispersed liquid particles, the second filter device preferably comprises pores having a size smaller than pores of the first filter device. The second filter device may include more than one pore size so that an aerosol of medicament having a variety of particle sizes is retained by the filter second device. The pores of the second filter device may also be sized to trap bacteria and particulate matter in the ambient air that is drawn into the second opening 78 when medicament in an attached vial is withdrawn.

The second filter device 84 may comprise particles, pellets, or beads of desiccant or molecular sieve material that retain, absorb, bind, or trap particles of an aerosol coming from an attached vial. Material for the second filter device includes, but is not limited to, highly porous amorphous silicon oxide, such as Silica Gel, aluminosilicates, such as zeolites, or combinations thereof. Advantageously, zeolites have porous structures with a polar surface that preferentially attract polar molecules with an uneven distribution of electron density, such as molecules of water and other liquids. Preferably, the desiccant or molecular sieve material is arranged or packed within the filter chamber 42 to form a network of convoluted pathways and surfaces that attract and retain liquid particles of medicament.

Figure 10:
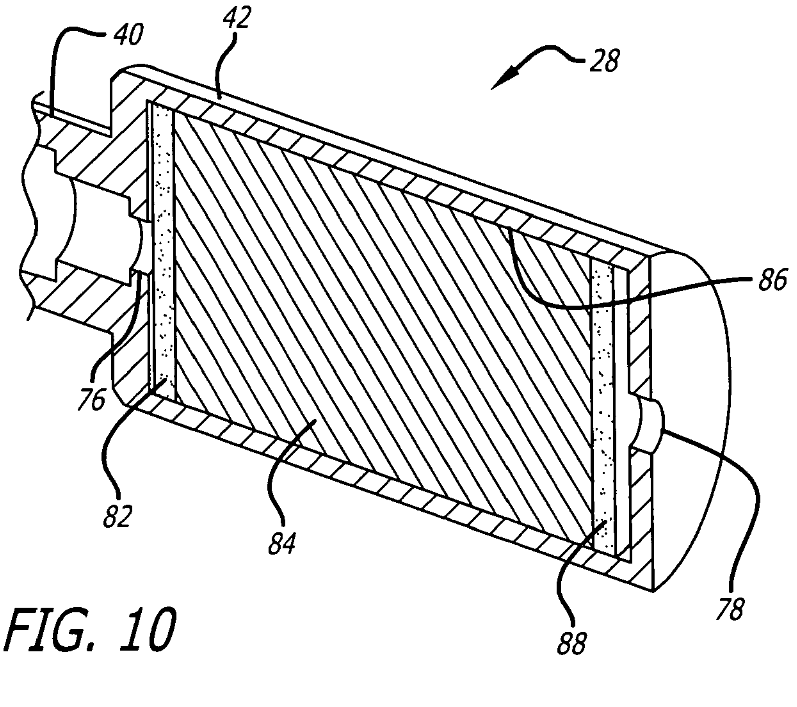
FIG. 10 is a perspective, cross-sectional view of a second embodiment of a filter apparatus showing a filter chamber having a first opening, a second opening, a first filter device, a second filter device, and a third filter device, the second filter device being located between the first and second filter devices.

In FIG. 10 there is shown a second embodiment of a filter apparatus 28 having a third filter device 88. In this embodiment, the third filter device is disposed between the second filter device 84 and the second opening 78 of the filter chamber 42, the second opening, also referred to as the vent opening 78, is exposed to the ambient environment surrounding the vial adapter 20. The outer periphery of the third filter device is attached to the inner cylindrical wall 86 of the filter chamber 42 such that fluids cannot pass around the outer periphery of the third filter device. The third filter device is configured to allow gas to pass in either direction through it, but prevents, or at least inhibits, bacteria and particulate matter in the ambient atmosphere surrounding the vial adapter 20 from reaching the second filter device 84 from the vent opening 78. Because the second filter device is shielded from external contaminants, more pores of the second filter device are available to absorb liquid particles of medicament.

The third filter device 88 can be a thin membrane or pad of porous material such as but not limited to polytetrafluoroethylene (PTFE) and other vinyl polymers. The third filter device may be identical to the first filter device 82 in thickness and material type. However, the third filter device may have a smaller pore size than the first filter device since the third filter device is not exposed to liquid particles of medicament that may clog smaller pores.

It will be appreciated that the present invention retains aerosols of medicament when accessing a vial of medicament. When a diluent is added to a vial to reconstitute medicament in dry or lyophilized form, air inside the vial is displaced by the added diluent and is vented without allowing particles of the medicament to contaminate the ambient atmosphere. When medicament is withdrawn or aspirated from the vial, air from the ambient atmosphere is drawn through the filter apparatus and into the vial interior, thereby equalizing air pressure in the vial with the ambient atmosphere without allowing bacteria and particulate matter in the air to contaminate the vial interior.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While variations have been described and shown, it is to be understood that these variations are merely exemplary of the present invention and are by no means meant to be limiting.

I claim:

1. A vented vial adapter for retaining aerosols when accessing a vial having a pierceable seal located over an opening of the vial, the adapter comprising:

a cannula having a medicament lumen and a vent lumen, the cannula having a relatively sharp tip to pierce the seal of the vial;

a body portion having:

a medicament port in fluid communication with the medicament lumen of the cannula, the medicament port configured to allow liquid to be introduced into and removed from the vial; and a vent port in fluid communication with the vent lumen of the cannula, the vent port configured to allow passage of filtered air to and from an atmosphere outside the vial, thereby allowing air pressure in the vial to equalize with the outside atmosphere when liquid is introduced into and removed from the vial;

a first filter device disposed between the vent lumen of the cannula and the vent port, the first filter device comprising pores having a diameter in the range of 0.2-3.0 microns and configured to allow passage of liquid dispersed in gas while blocking non-dispersed liquid;

a second filter device disposed between the first filter device and the vent port, the second filter device configured to absorb liquid dispersed in gas; and a third filter device disposed between the second filter device and the vent port, the third filter device configured to inhibit the passage of bacteria, a pore size of the third filter device being smaller than 0.2 microns.

2. The vial adapter of claim 1 wherein the first filter device comprises pores having a first pore size, and the second filter device comprises pores having a second pore size that is different than the first pore size.

3. The vial adapter of claim 2 wherein the first filter is hydrophobic and has a pore size selected to prevent the passage of liquid through the first filter, whereby the first filter prevents wetting out the second filter.

4. The vial adapter of claim 1 wherein the second filter device comprises a desiccant configured to absorb liquid particles.

5. The vial adapter of claim 1 wherein the second filter device comprises a molecular sieve having pores sized to trap liquid particles.

6. The vial adapter of claim 1 wherein the second filter device comprises pores having a polar surface adapted to attract polar molecules.

7. The vial adapter of claim 1, wherein the first filter device is configured to prevent passage of bacteria.

8. The vial adapter of claim 1, wherein the first and third filter devices are membranes made of vinyl polymer.

9. The vial adapter of claim 8, wherein the vinyl polymer is polytetrafluoroethylene.

10. A vented vial adapter for retaining aerosols when accessing a vial having a pierceable seal located over an opening of the vial, the adapter comprising:

a flexible attachment device configured to engage the vial for secure mounting of the vial adapter to the vial;

a cannula on the attachment device, the cannula having a sharpened tip configured to pierce the seal of the vial, a vent opening adjacent the sharpened tip, a slot, and a medicament opening on the slot, the vent opening leading to a vent lumen extending through the cannula, the medicament opening leading to a medicament lumen extending through the cannula;

a body portion having a valve in fluid communication with the medicament lumen of the cannula, the valve biased to a closed orientation and configured to allow liquid to be introduced into and removed from the vial when the valve is actuated to an open orientation; and an elongate filter chamber having a first opening and a second opening, the first opening in fluid communication with the vent lumen of the cannula, the filter chamber containing a first filter device and a second filter device and a third filter device, the first filter device disposed between the first opening and the second filter device and comprising pores having a diameter in the range of 0.2-3.0 microns and configured to allow passage of liquid dispersed in gas to the second filter device while blocking non-dispersed liquid, the second filter device disposed between the first filter device and the second opening and configured to absorb liquid dispersed in gas, the third filter device disposed between the second filter device and the second opening in the filter chamber and configured to prevent passage of bacteria, a pore size of the third filter device being smaller than 0.2 microns.

11. The vial adapter of claim 10 wherein the first filter device comprises pores having a first pore size, and the second filter device comprises pores having a second pore size that is different than the first pore size.

12. The vial adapter of claim 11 wherein the first filter is hydrophobic and has a pore size selected to prevent the passage of liquid through the first filter, whereby the first filter prevents wetting out the second filter.

13. The vial adapter of claim 10 wherein the second filter device comprises a desiccant configured to absorb liquid particles.

14. The vial adapter of claim 10 wherein the second filter device comprises a molecular sieve having pores sized to trap liquid particles.

15. The vial adapter of claim 10 wherein the second filter device comprises pores having a polar surface adapted to attract polar molecules.

16. A vented vial adapter for retaining aerosols when accessing a vial having a pierceable seal located over an opening of the vial, the adapter comprising:

an attachment device configured to engage the vial for mounting of the vial adapter to the vial;

a cannula on the attachment device, the cannula having a sharpened tip configured to pierce the seal of the vial, a vent opening adjacent the sharpened tip, a slot, and a medicament opening on the slot, the vent opening leading to a vent lumen extending through the cannula, the medicament opening leading to a medicament lumen extending through the cannula; and an elongate filter chamber having a first opening and a second opening, the first opening in fluid communication with the vent lumen of the cannula, the second opening being exposed to atmosphere, the filter chamber containing a first filter device, a second filter device and a third filter device, the first filter device disposed between the first opening and the second filter device and comprising pores having a diameter in the range of 0.2-3.0 microns and configured to allow passage of liquid dispersed in gas to the second filter device while blocking non-dispersed liquid, the second filter device disposed between the first filter device and the second opening and configured to absorb liquid dispersed in gas, the third filter device disposed between the second filter device and the second opening in the filter chamber and configured to prevent passage of bacteria, a pore size of the third filter device being smaller than 0.2 microns.

17. The vial adapter of claim 16, wherein the first filter device is configured to prevent passage of bacteria.

18. The vial adapter of claim 17, wherein the first and third filter devices are membranes made of vinyl polymer.

19. The vial adapter of claim 18, wherein the vinyl polymer is polytetrafluoroethylene.

* * * * *